United States Patent
Badr et al.

(10) Patent No.: US 10,801,066 B2
(45) Date of Patent: Oct. 13, 2020

(54) DETERMINATION OF RISK FOR DEVELOPMENT OF CARDIOVASCULAR DISEASE BY MEASURING URINARY LEVELS OF PODOCIN AND NEPHRIN MESSENGER RNA

(71) Applicant: AMERICAN UNIVERSITY OF BEIRUT, Beirut (LB)

(72) Inventors: Kamal F. Badr, Beirut (LB); Assaad A Eid, Beirut (LB); Robert H. Habib, Beirut (LB)

(73) Assignee: American University of Beirut, Beirut (LB)

(*) Notice: Subject to any disclaimer, the term of this patent is extended or adjusted under 35 U.S.C. 154(b) by 134 days.

(21) Appl. No.: 14/847,946

(22) Filed: Sep. 8, 2015

(65) Prior Publication Data
US 2016/0068911 A1 Mar. 10, 2016

Related U.S. Application Data

(60) Provisional application No. 62/046,455, filed on Sep. 5, 2014.

(51) Int. Cl.
*C12Q 1/6883* (2018.01)

(52) U.S. Cl.
CPC ..... *C12Q 1/6883* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,910,323 B2 | 3/2011 | Hellerstein | 435/14 |
| 8,105,840 B2 | 1/2012 | Hara et al. | 436/86 |
| 2004/0058395 A1 | 3/2004 | Hara | 435/7.2 |
| 2006/0008804 A1 | 1/2006 | Chibout et al. | 435/6 |
| 2011/0144914 A1 | 6/2011 | Harrington | 702/19 |
| 2012/0142544 A1 | 6/2012 | Hare et al. | 506/7 |
| 2012/0301402 A1 | 11/2012 | Chotani et al. | 424/9.2 |
| 2012/0322087 A1 | 12/2012 | Hara et al. | 435/7.92 |
| 2014/0127704 A1 | 5/2014 | Chen et al. | 435/6.13 |

FOREIGN PATENT DOCUMENTS

| | | | |
|---|---|---|---|
| EP | 2 019 318 | 1/2009 | G01N 33/50 |
| WO | WO 01/80712 A2 | 11/2001 | C12Q 1/68 |
| WO | WO 2007/131345 | 11/2007 | C12Q 1/68 |
| WO | WO 2008/118148 A2 | 10/2008 | A61K 38/17 |
| WO | WO 2013/134733 | 9/2013 | A61B 18/14 |
| WO | WO 2014/142649 | 9/2014 | G01N 33/68 |

OTHER PUBLICATIONS

Enard et al. (Science 2002 vol. 296 p. 340).*
Cobb et al (Crit Care Med 2002 vol. 30 p. 2711).*
Cheung et al (Nature Genetics 2003 vol. 33 p. 422).*
Wu (Journal of pathology 2001 vol. 195 p. 53).*
Newton et al (Journal of Computational Biology 2001 vol. 8 p. 37).*
Ohira et al. (Cancer Cell Apr. 2005 vol. 7 p. 337) (Year: 2005).*
Cheung et al (Nature Genetics 2003 vol. 33 p. 422) (Year: 2003).*
International Search Report issued in a corresponding foreign application, pp. 1-6 (dated May 12, 2016).
Zhang, Z., et al., "Combination therapy with $AT_1$ blocker and vitamin D analog markedly ameliorates diabetic nephropathy: blockade of compensatory renin increase" *Proc. Natl. Acad. Sci.* 105(41): 15896-15901 (2008).
EP Extended Search Report and Search Opinion, EP App. 15844203.8.3, pp. 1-9, (dated Jan. 17, 2018).
Zanone M M et al: "Expression of nephrin by human pancreatic islet endothelial cells," Diabetologia ; Clinical and Experimental Diabetes and Metabolism, Springer, Berlin, DE, vol. 48, No. 9, Sep. 1, 2005, pp. 1789-1797.
Marshall, Sally M: "Recent advances in diabetic nephropathy," Clinical Medicine, Journal of the Royal College of Physicians, May 1, 2004, pp. 277-282.
Wang, Cheng et al: "New urinary biomarkers for diabetic kidney disease," Biomarker Research, Biomed Central Ltd, London, UK, vol. 1, No. 1, Feb. 4, 2013 , p. 9.

* cited by examiner

*Primary Examiner* — Katherine D Salmon
(74) *Attorney, Agent, or Firm* — J. Peter Paredes; David G. Rosenbaum; Rosenbaum IP, P.C.

(57) ABSTRACT

A method for a determining of risk for development of cardiovascular disease by measuring levels of the at least gene of interest is disclosed. The method may identify subjects with moderate albuminuria and diagnosis or predict cardiovascular disease several years before either of these outcomes is detectable by present methodologies.

9 Claims, 11 Drawing Sheets

| Biomarker | Visit 1 | | | Visit 2 | | | Visit 3 | | |
|---|---|---|---|---|---|---|---|---|---|
| | Mean±SD | Median | (IQR) | Mean±SD | Median | (IQR) | Mean±SD | Median | (IQR) |
| All Subjects (N=106) | | | | | | | | | |
| Podocin (million copies) | 0.78±0.39 | 0.65 | (0.45,1.1) | 4.6±1.3 | 4.3 | (3.8,5.8) | 10.8±2.9 | 10.2 | (8.6,13.2) |
| Nephrin (million copies) | 1.76±0.75 | 1.80 | (1.10,2.50) | 3.6±1.3 | 3.7 | (2.3,4.8) | 8.7±1.8 | 8.3 | (7.3,10.3) |
| AER (mcg/mg) | 8.8±2.3 | 9.5 | (6.5,10.5) | 126±43 | 105 | (90,166) | 804±196 | 866 | (679, 965) |
| ΔPodocin # | | | | 1.05±0.35 | 1.04 | (0.82,1.23) | 1.53±0.60 | 1.45 | (1.07,1.81) |
| ΔNephrin # | | | | 0.50±0.25 | 0.51 | (0.30,0.66) | 1.05±0.35 | 0.97 | (0.84,1.20) |
| ΔAER # | | | | 32±14 | 27 | (22,40) | 120±40 | 121 | (92,144) |
| No-CVD (N=50) | | | | | | | | | |
| Podocin (million copies) | 0.45±0.12 | 0.45 | (0.35,0.54) | 3.7±0.8 | 3.8 | (3.1,4.2) | 8.1±1.2 | 8.4 | (7.3,9.1) |
| Nephrin (million copies) | 1.10±0.36 | 1.10 | (0.90,1.40) | 2.5±0.7 | 2.3 | (1.9,2.8) | 7.3±0.9 | 7.3 | (6.7,8.1) |
| AER (mcg/mg) | 8.5±2.2 | 8.0 | (6.5,10.5) | 97±12 | 98 | (88,105) | 872±124 | 878 | (787,965) |
| ΔPodocin # | | | | 0.88±0.28 | 0.87 | (0.67,1.02) | 1.10±0.24 | 1.07 | (0.94,1.26) |
| ΔNephrin # | | | | 0.37±0.22 | 0.33 | (0.20,0.51) | 0.89±0.19 | 0.91 | (0.75,1.00) |
| ΔAER # | | | | 24±4 | 24 | (20,27) | 123±25 | 121 | (102,144) |
| CVD (N=56) | | | | | | | | | |
| Podocin (million copies) | 1.07±0.31 | 1.10 | (0.80,1.30) | 5.5±1.1 | 5.8 | (4.5,6.4) | 13.1±1.8 | 12.9 | (12.3,14.3) |
| Nephrin (million copies) | 2.36±0.44 | 2.45 | (1.95,2.80) | 4.6±0.7 | 4.8 | (4.1,5.1) | 9.9±1.4 | 10.3 | (8.7,10.9) |
| AER (mcg/mg) | 9.1±2.3 | 9.8 | (6.5,11.1) | 151±45 | 166 | (101,180) | 744±227 | 791 | (554,958) |
| ΔPodocin # | | | | 1.20±0.33 | 1.17 | (1.05,1.33) | 1.91±0.57 | 1.80 | (1.57,2.13) |
| ΔNephrin # | | | | 0.61±0.22 | 0.61 | (0.49,0.72) | 1.20±0.40 | 1.14 | (0.92,1.32) |
| ΔAER # | | | | 39±16 | 39 | (28,48) | 117±50 | 119 | (79,144) |

FIG. 2A

| Factor | CVD (N=56) | | | | | No-CVD (N=50) | | | | | P-value |
|---|---|---|---|---|---|---|---|---|---|---|---|
| | mean | sd | median | min | max | mean | sd | median | min | max | |
| Age (years) | 46.2 | 9.8 | 49.0 | 21.0 | 62.0 | 46.8 | 7.9 | 46 | 31 | 61 | 0.696 |
| Ht (cm) | 167 | 11 | 166 | 143 | 193 | 172 | 7 | 173 | 154 | 190 | 0.005 |
| Wt (kg) | 78 | 17 | 76 | 44 | 119 | 83 | 9 | 84 | 62 | 98 | 0.092 |
| BSA (m$^2$) | 1.90 | .26 | 1.84 | 1.34 | 2.47 | 1.99 | 0.13 | 2.01 | 1.63 | 2.21 | 0.029 |
| BMI (kg/m$^2$) | 27.9 | 3.8 | 27.6 | 20.1 | 35.6 | 28.0 | 2.9 | 28.3 | 21.6 | 33.7 | 0.858 |
| SBP (mmHg) | 129.4 | 10.3 | 130 | 110 | 145 | 130.2 | 8.7 | 130 | 110 | 150 | 0.671 |
| DBP (mmHg) | 68.5 | 7.2 | 70 | 52 | 80 | 69.6 | 7.5 | 70 | 60 | 85 | 0.472 |
| T-since-DM (yrs) | 6.1 | 1.4 | 6 | 4 | 9 | 6.5 | 1.5 | 6 | 4 | 9 | 0.156 |
| Biomarkers | | | | | | | | | | | |
| Podocin | 1.07 | 0.31 | 1.1 | 0.4 | 1.7 | 0.45 | 0.12 | 0.4 | 0.2 | 0.7 | 0.000 |
| nephrin | 2.36 | 0.44 | 2.5 | 1.5 | 3.1 | 1.10 | 0.36 | 1.1 | 0.3 | 2.1 | 0.000 |
| Triglycerides (mmol/L) | 1.37 | 0.45 | 1.4 | 0.7 | 2.6 | 1.97 | 0.71 | 1.9 | 0.8 | 3.8 | 0.000 |
| Total Cholest (mmol/L) | 7.37 | 6.38 | 6.6 | 4.2 | 53.0 | 7.12 | 1.28 | 7.3 | 4.3 | 9.6 | 0.789 |
| HDL (mmol/L) | 0.95 | 0.31 | 0.9 | 0.4 | 1.5 | 1.17 | 0.38 | 1.1 | 0.5 | 1.9 | 0.001 |
| LDL (mmol/L) | 3.25 | 0.66 | 3.3 | 1.8 | 4.5 | 3.71 | 0.65 | 3.8 | 2.2 | 4.9 | 0.000 |
| AER (mg/g creatinine) | 9.10 | 2.32 | 9.8 | 5.6 | 12.8 | 8.54 | 2.18 | 8.0 | 5.6 | 12.3 | 0.199 |
| serum Cr (mg/dL) | 1.11 | 0.16 | 1.1 | 0.9 | 1.6 | 1.12 | 0.16 | 1.1 | 0.9 | 1.6 | 0.906 |
| eGFR (ml/min) | 75.3 | 14.3 | 74.5 | 44.6 | 102.7 | 74.3 | 14.1 | 74.6 | 44.9 | 99.8 | 0.713 |
| HbA1C (%) | 7.30 | 0.48 | 7.3 | 6.4 | 8.1 | 7.35 | 0.52 | 7.4 | 6.4 | 8.4 | 0.466 |
| Categorical | n | % | | | | n | % | | | | P-value |
| Male | 49 | 87.5% | | | | 43 | 86.0% | | | | 0.820 |
| Wt-Categ (0,1,2) | | | | | | | | | | | 0.463 |
| Normal | 8 | 16.0% | | | | 14 | 25.9% | | | | |
| Overweight | 27 | 54.0% | | | | 26 | 48.1% | | | | |
| Obese | 15 | 30.0% | | | | 14 | 25.9% | | | | |
| Smoking (0,1,2) | | | | | | | | | | | 0.302 |
| Never | 22 | 44.0% | | | | 21 | 37.5% | | | | |
| Previous | 10 | 20.0% | | | | 7 | 12.5% | | | | |
| Current | 18 | 36.0% | | | | 28 | 50.0% | | | | |
| Hypertension | 27 | 48.2% | | | | 30 | 60.0% | | | | 0.224 |
| Medication (Any) | 47 | 83.9% | | | | 44 | 88.0% | | | | 0.548 |
| Oral hypoglycemics | 47 | 83.9% | | | | 43 | 86.0% | | | | 0.766 |
| ACE Inhibitor | 20 | 35.7% | | | | 15 | 30.0% | | | | 0.532 |
| ARB | 10 | 17.9% | | | | 11 | 22.0% | | | | 0.593 |
| Statin | 23 | 41.1% | | | | 11 | 22.0% | | | | 0.036 |

FIG. 2B

|  | Visit #1 | | Visit #2 | | Visit #3 | |
| --- | --- | --- | --- | --- | --- | --- |
|  | NoCVD | CVD | NoCVD | CVD | NoCVD | CVD |
|  | Mean | Mean | Mean | Mean | Mean | Mean |
| Age (yrs) | 47 | 46 | 51 | 50 | 54 | 53 |
| Ht (cm) | 172 | 167 | 172 | 167 | 172 | 167 |
| Wt(kg) | 83 | 78 | 84 | 78 | 81 | 78 |
| BSA (m$^2$) | 1.99 | 1.90 | 2.09 | 1.90 | 1.97 | 1.90 |
| BMI (kg/m$^2$) | 28.0 | 27.9 | 28.2 | 28.1 | 27.5 | 28.1 |
| SBP (mmHg) | 130 | 129 | 130 | 131 | 130 | 132 |
| DBP (mmHg) | 70 | 69 | 71 | 70 | 71 | 70 |
| T-since-DM (yrs) | 6.5 | 6.1 | 10.2 | 10.1 | 13.6 | 12.6 |
| Biomarkers | | | | | | |
| Podocin | .45 | 1.07 | 3.75 | 5.48 | 8.12 | 13.10 |
| nephrin | 1.10 | 2.36 | 2.49 | 4.61 | 7.30 | 9.94 |
| Triglycerides (mmol/L) | 2.0 | 1.4 | 2.1 | 1.5 | 2.3 | 1.9 |
| Total Cholesterol (mmol/L) | 7.1 | 7.4 | 7.2 | 7.1 | 7.4 | 7.2 |
| HDL (mmol/L) | 1.2 | 1.0 | 1.4 | 1.0 | 1.4 | 1.2 |
| LDL (mmol/L) | 3.7 | 3.2 | 3.7 | 3.3 | 4.0 | 3.7 |
| UACR (mg/g) | 8.5 | 9.1 | 97.4 | 151.0 | 871.8 | 743.6 |
| serum Cr (mg/dL) | 1.1 | 1.1 | 1.5 | 1.8 | 2.0 | 3.2 |
| eGFR | 74.25 | 75.28 | 52.61 | 42.30 | 37.09 | 22.11 |
| HbA1C (%) | 7.4 | 7.3 | 7.5 | 7.6 | 8.0 | 8.1 |
| Categorical | % | % | % | % | % | % |
| Male | 86.0% | 87.5% | 86.0% | 87.5% | 86.0% | 87.5% |
| Wt-Categ (0,1,2) | | | | | | |
|   Normal | 16.0% | 25.9% | 16.0% | 19.6% | 14.0% | 19.6% |
|   Overweight | 54.0% | 48.1% | 62.0% | 50.0% | 72.0% | 50.0% |
|   Obese | 30.0% | 25.9% | 22.0% | 30.4% | 14.0% | 30.4% |
| Smoking (0,1,2) | | | | | | |
|   Never | 44.0% | 37.5% | 44.0% | 37.5% | 44.0% | 37.5% |
|   Previous | 20.0% | 12.5% | 10.0% | 12.5% | 34.0% | 12.5% |
|   Current | 36.0% | 50.0% | 46.0% | 50.0% | 22.0% | 50.0% |
| Hypertension | 60.0% | 48.2% | 50.0% | 64.3% | 66.0% | 64.3% |
| Medication (Any) | 88.0% | 83.9% | 100.0% | 94.6% | 100.0% | 96.4% |
| Oral hypoglycemics | 86.0% | 83.9% | 100.0% | 96.4% | 100.0% | 96.4% |
| ACE Inhibitor | 30.0% | 35.7% | 32.0% | 58.9% | 52.0% | 58.9% |
| ARB | 22.0% | 17.9% | 28.0% | 26.8% | 48.0% | 26.8% |
| Statin | 22.0% | 41.1% | 0.0% | 48.2% | 54.0% | 48.2% |

FIG. 2C

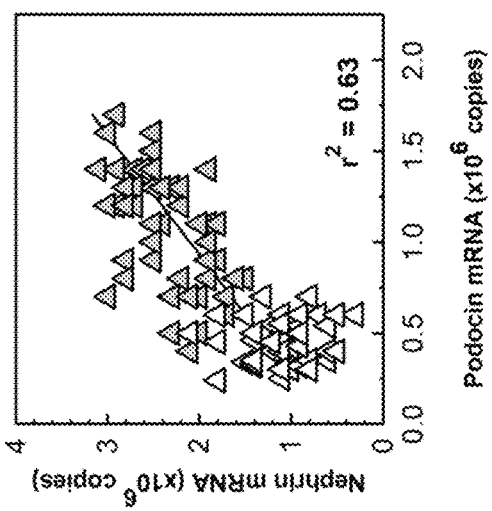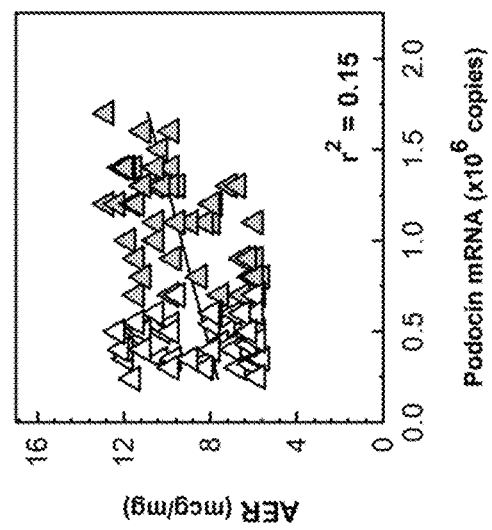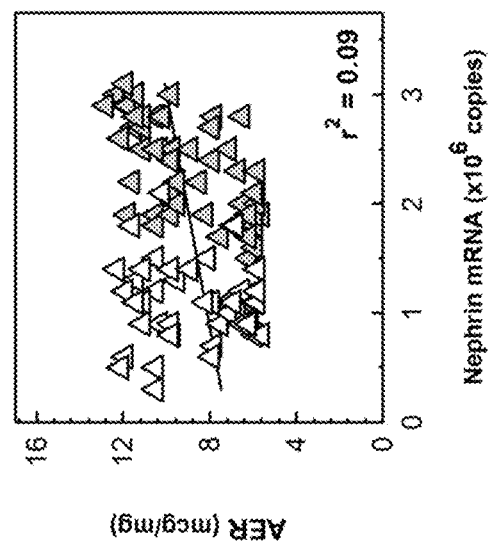
FIG. 4A
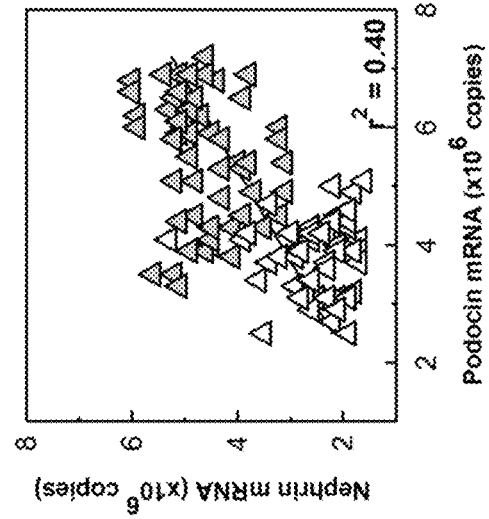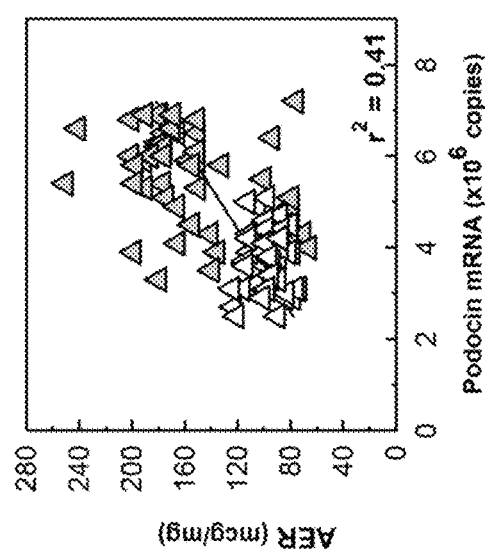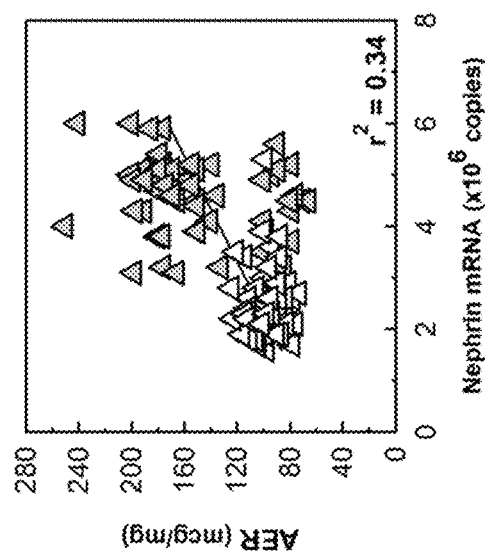
FIG. 4B

| Factor | Baseline Podocin Terciles (Visit 1) | | | | | | Baseline Nephrin Terciles (Visit 1) | | | | | |
|---|---|---|---|---|---|---|---|---|---|---|---|---|
| | Low | | Intermediate | | High | | Low | | Intermediate | | High | |
| N | 36 | | 35 | | 35 | | 36 | | 35 | | 35 | |
| Continuous | Mean | ± SD | Mean | ± SD | Mean | ± SD | Mean | ± SD | Mean | ± SD | Mean | ± SD |
| Age (yrs) | 47 | ± 8.2 | 45.6 | ± 10.0 | 46.9 | ± 8.6 | 46.4 | ± 8.1 | 46 | ± 9.7 | 47.1 | ± 9.0 |
| BSA (m²) | 1.98 | ± 0.13 | 1.97 | ± 0.22 | 1.87 | ± 0.26 | 1.99 | ± 0.13 | 1.94 | ± 0.23 | 1.9 | ± 0.26 |
| BMI (kg/m²) | 27.8 | ± 2.90 | 27.9 | ± 3.4 | 28.2 | ± 4.0 | 28.2 | ± 2.7 | 27.9 | ± 3.6 | 27.8 | ± 3.9 |
| SBP (mmHg) | 131 | ± 9 | 126 | ± 9 | 133 | ± 9 b | 130 | ± 9 | 123 | ± 9 a | 136 | ± 7 a,b |
| DBP (mmHg) | 70 | ± 8 | 66 | ± 7 | 71 | ± 6 b | 69.4 | ± 7.2 | 66.1 | ± 7.7 | 71.7 | ± 6.0 b |
| TG (mmol/l) | 2 | ± 0.7 | 1.5 | ± 0.6 a | 1.4 | ± 0.4 a | 1.93 | ± 0.70 | 1.61 | ± 0.68 | 1.4 | ± 1.47 a,b |
| Total Cholesterol (mmol/l) | 6.9 | ± 1.3 | 8.1 | ± 8.0 | 6.7 | ± 1.4 | 7.26 | ± 1.21 | 7.57 | ± 8.03 | 6.93 | ± 1.40 |
| HDL (mmol/l) | 1.09 | ± 0.37 | 1.11 | ± 0.39 | 0.97 | ± 0.30 | 1.13 | ± 0.36 | 1 | ± 0.41 | 1.04 | ± 0.28 |
| LDL (mmol/l) | 3.7 | ± 0.7 | 3.4 | ± 0.6 | 3.2 | ± 0.7 a | 3.7 | ± 0.7 | 3.3 | ± 0.7 | 3.4 | ± 0.6 |
| HbA1C (%) | 7.4 | ± 0.5 | 7.2 | ± 0.5 | 7.4 | ± 0.5 | 7.3 | ± 0.5 | 7.2 | ± 0.5 | 7.5 | ± 0.4 b |
| sCR (mmol/l) | 97.2 | ± 17.0 | 97.2 | ± 8.8 | 106.1 | ± 8.8 b | 97.2 | ± 17.0 | 97.2 | ± 17.7 | 106.1 | ± 8.8 a,b |
| Podocin mRNA | 0.39 | ± 0.07 | 0.68 | ± 0.13 a | 1.27 | ± 0.17 a,b | 0.45 | ± 0.11 | 0.68 | ± 0.28 a | 1.2 | ± 0.27 a,b |
| Nephrin mRNA | 1.1 | ± 0.35 | 1.7 | ± 0.71 a | 2.5 | ± 0.37 a,b | 0.9 | ± 0.2 | 1.7 | ± 0.3 a | 2.6 | ± 0.2 a,b |
| AER | 8.4 | ± 2.32 | 8.0 | ± 2.10 | 10.2 | ± 1.75 b | 8.3 | ± 2.2 | 8.1 | ± 2.2 | 10 | ± 2.0 a,b |
| Categorical | N | (%) | N | (%) | N | (%) | N | (%) | N | (%) | N | (%) |
| Male | 12 | 33% | 16 | 46% | 18 | 51% | 14 | 38.90% | 14 | 40.00% | 18 | 51.40% |
| Smoking | 31 | 86% | 32 | 91% | 29 | 83% | 32 | 88.90% | 29 | 82.90% | 31 | 88.60% |
| Hypertension | 5 | 14% | 8 | 23% | 4 | 11% | 8 | 22.20% | 3 | 8.60% | 6 | 17.10% |
| Oral hypoglycemics | 22 | 61% | 15 | 43% | 20 | 57% | 20 | 55.60% | 13 | 37.10% | 24 | 68.6% b |
| Insulin | 31 | 86% | 29 | 83% | 30 | 86% | 33 | 91.70% | 27 | 77.10% | 30 | 85.70% |
| ACE Inhibitor | 11 | 31% | 8 | 23% | 16 | 46% | 12 | 33.30% | 5 | 14.30% | 18 | 51.4% b |
| ARB | 10 | 28% | 4 | 11% | 7 | 20% | 7 | 19.40% | 4 | 11.40% | 10 | 28.60% |
| Statin | 9 | 25% | 9 | 26% | 16 | 46% | 9 | 25.00% | 9 | 25.70% | 16 | 45.70% |
| Outcomes | N | (%) | N | (%) | N | (%) | N | (%) | N | (%) | N | (%) |
| CRVD | 1 | 3% | 19a | (54%) a | 35a | (100%) a,b | 2 | 0.00% | 21 | 60.00% | 34 | 97.1% b |
| CAD | 1 | 3% | 12a | (34%) a | 26 | (74%) a,b | 2 | 0.00% | 14 | 40.00% | 25 | 71.4% b |
| AF | 1 | 3% | 14a | (40%) a | 23 | (66%) a | 2 | 0.00% | 14 | 40.00% | 24 | 68.6% b |
| PVD | 1 | 3% | 9a | (26%) a | 8 | (23%) a | 2 | 0.00% | 7 | 20.00% | 11 | 31.40% |

FIG. 5A

| Biomarker | N | B | SE | p value | Adjusted HR (95% CI) |
|---|---|---|---|---|---|
| | | | | | |
| Continuous Values | | | | | |
| AER (mcg/mg) | 106 | .155 | .076 | .041 | 1.17 (1.01-1.36) |
| Podocin mRNA ($10^6$ copies) | 106 | 2.767 | .492 | .000 | 15.9 (6.1-41.8) |
| Nephrin mRNA ($10^6$ copies) | 106 | 2.030 | .361 | .000 | 7.61 (3.75-15.5) |
| | | | | | |
| Two Categories[#] | | | | | |
| AER | 52/54 | .502 | .329 | .127 | 1.65 (0.87-3.14) |
| Podocin mRNA | 53/53 | 2.507 | .506 | .000 | 12.3 (4.55-33.1) |
| Nephrin mRNA | 52/54 | 2.767 | .520 | .000 | 15.9 (5.74-44.0) |
| | | | | | |
| Three Categories | | | | | |
| AER | | | | .289 | |
|   Low | 34 | | | | 1.0 (ref) |
|   Intermediate | 32 | .426 | .430 | .322 | 1.53 (0.66-3.55) |
|   High | 40 | .610 | .390 | .118 | 1.84 (0.86-3.95) |
| | | | | | |
| Podocin terciles | | | | .000 | |
|   Low | 36 | | | .000 | 1.0 (ref) |
|   Intermediate | 35 | 3.003 | 1.049 | .004 | 20.1 (2.58-157.4) |
|   High | 35 | 4.086 | 1.039 | .000 | 59.5 (7.8-456.2) |
| | | | | | |
| Nephrin terciles * | | * | * | * | * |

FIG. 5B

A) Albuminuria Groups

B) Podocin mRNA Terciles *

DETERMINATION OF RISK FOR DEVELOPMENT OF CARDIOVASCULAR DISEASE BY MEASURING URINARY LEVELS OF PODOCIN AND NEPHRIN MESSENGER RNA

CROSS-REFERENCE TO RELATED APPLICATIONS

The present application claims the benefit of priority to U.S. Provisional Application Ser. No. 62/046,455, filed Sep. 5, 2014, herein incorporated by reference in its entirety.

BACKGROUND

The invention generally relates to disease, and more specifically to diagnosing disease.

In diabetic and non-diabetic individuals who develop vascular disease, a large body of high-quality evidence has established a direct and continuous relationship between Albumin Excretion Rates (AER) and adverse renal and CV outcomes, establishing AER as an independent predictor of CVD. In fact, it was previously demonstrated, in a large population of initially "normoalbuminuric" diabetics, that any increase in albumin excretion is associated with a continuous nonlinear relationship with CVD development over a mean follow-up period of 9.2 years. Even minute increases in measurable albuminuria (e.g. from <1 mcg/min to 1-2 mcg/min) conferred a significant increase in risk. Because it is such a powerful and independent predictor of CVD, moderate albuminuria (previously microalbuminuria) has been incorporated as a major risk factor in several national and international guidelines for the treatment of hypertension and other vascular diseases, and in the calculation of mortality risk in Type II diabetic patients.

The mechanisms linking albumin excretion to cardiovascular risk have been the subject of numerous reviews. Available evidence places endothelial cell injury as a common event occurring simultaneously in systemic and renal vasculature, but detectable only through its measurable functional effects at the glomerulus, as shown in FIG. 1. Albuminuria is invariably accompanied by injury to the glomerular epithelial cell (podocyte) across which filtered plasma reaches the proximal tubule.

The present invention attempts to solve these problems, as well as others.

SUMMARY OF THE INVENTION

Provided herein are systems and method for a determining of risk for development of cardiovascular disease by measuring levels of the at least gene of interest is selected from the group consisting of nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 2A is a table showing the change in biomarker per year of Visits 2 and 3 relative to Visit 1. All comparisons across visits were significantly different ($P<0.05$). Interquartile Range (IQR) and Albumin Excretion Rate (AER) at (mcg/mg creatinine)

FIG. 2B is a table showing the comparison of Visit 1 baseline characteristics of patients who subsequently developed or did not develop CVD.

FIG. 2C is a table showing the progression of clinical and biochemical parameters at 4 and 7 years following the initial visit in patients who developed and did not develop CVD.

FIG. 4A is a graph of the Baseline or Visit 1 levels of urinary nephrin and podocin mRNA levels that were highly correlated ($r^2=0.63$), but neither was well correlated to the baseline albuminuria levels ($r^2=0.15$ and 0.09 for podocin and nephrin, respectively).

FIG. 4B-4C is a graph showing the increases in podocin and nephrin mRNA longitudinally over time appeared to track each other fairly closely and remained well correlated despite the substantial rise in absolute levels ($r^2=0.40$ and 0.37 at visits 2 and 3, respectively).

FIG. 5A is a table where sCR: serum creatinine; ARB: angiotensin receptor blocker; CRVD: Cerebrovascular Disease (stroke); CAD=coronary artery disease; AF=Atrial Fibrillation;

PVD=peripheral vascular disease. $^{a}=P<0.05$ compared to Low tercile; $^{b}=P<0.05$ compared to Intermediate tercile.

FIG. 5B is a table where N=number of subjects; B (SE)=cox regression coefficient (standard error); HR (95% CI)=hazard ratio (95% confidence interval). Data is adjusted for the following Visit 1 factors: gender, age, body mass index, smoking, hypertension (yes/no), statin use (yes/no), systolic and diastolic blood pressure, triglyceride, low and high density lipoprotein, and hemoglobin A1c levels. #: biomarker groups divided to sub-cohorts based on the median visit 1 value; *: not calculated since no subjects in the low Nephrin tercile group had documented CVD during follow-up.

Figure 6A:
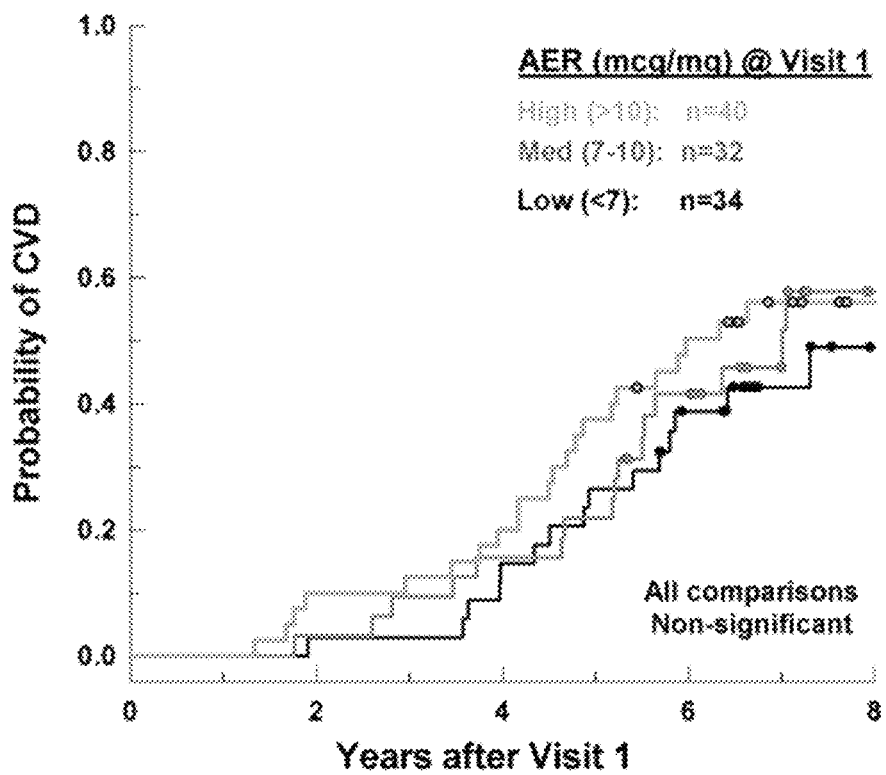
Figure 6B:
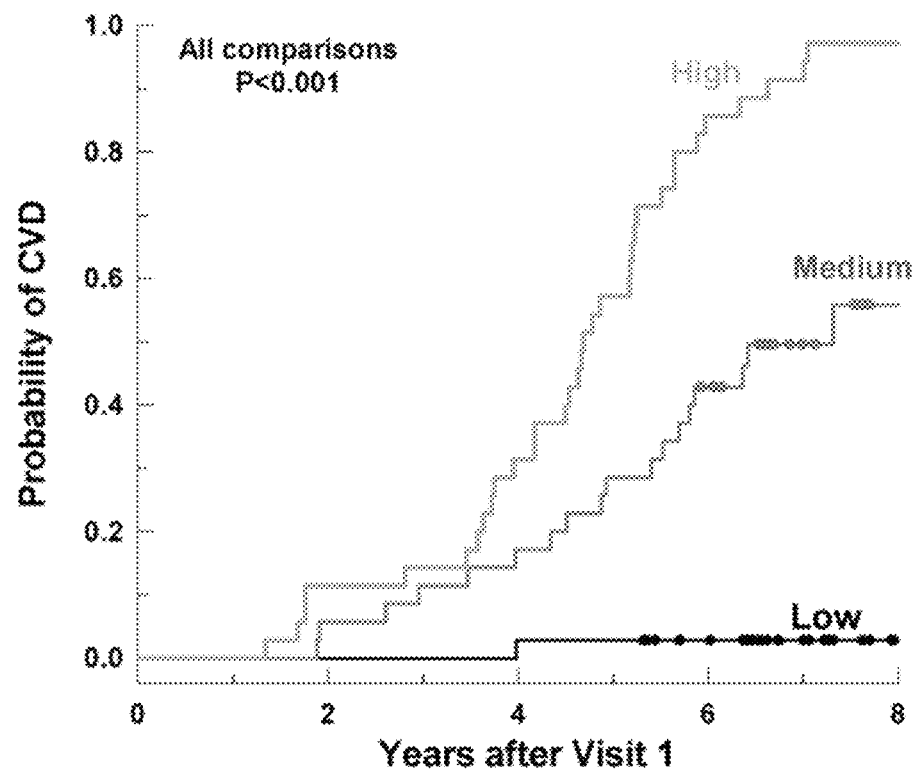
Figure 6C:
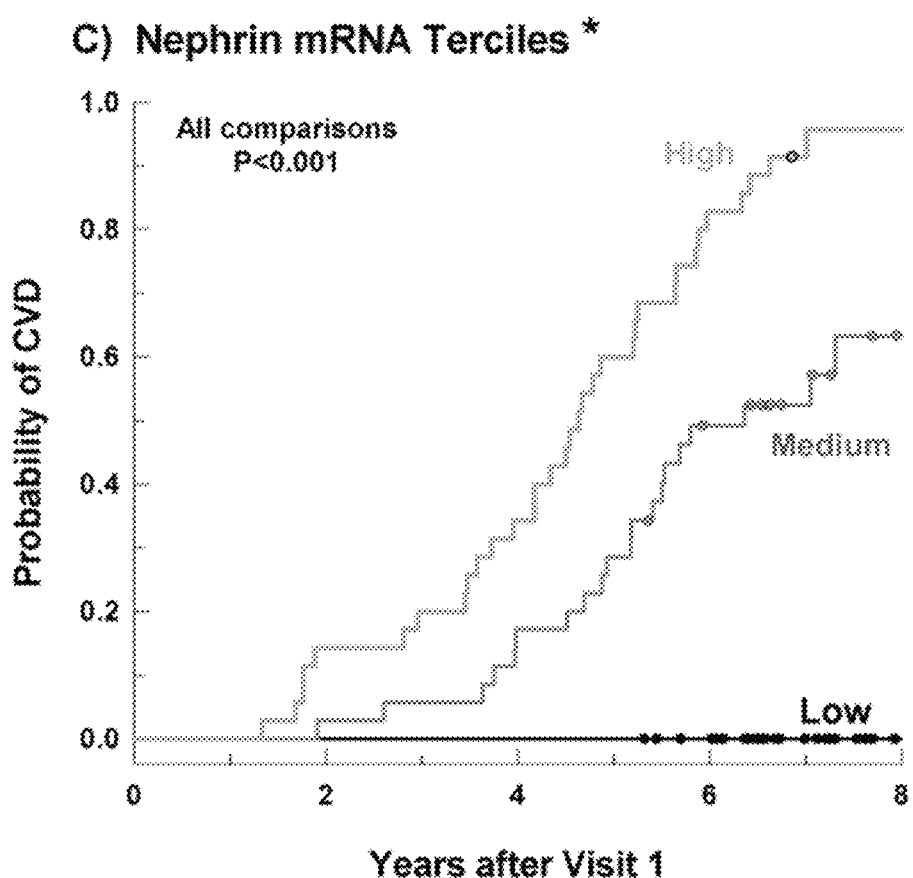

FIG. 6A-6C are graphs showing the Correlations Among Urinary Biomarkers and Relation to Cardiovascular Disease: The data provides evidence for the superiority of nephrin/podocin mRNA over AER as a faithful indicator of CV injury over time.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

Definitions

As used herein, "disease prediction," "prediction" or similar terms, means to predict the occurrence of disease before it occurs.

As used herein, "diagnosis" or "diagnostic" means a prediction of the type of disease or condition from a set of marker values and/or patient symptoms.

As used herein, "prognosis" or "prognostic" means to predict disease progression at a future point in time from one or more indicator values.

As used herein, "sample" means any sample of biological material derived from a subject, such as, but not limited to, blood, plasma, mucus, biopsy specimens and fluid, urine, semen, vaginal fluid, which has been removed from the body of the subject. The sample which is tested according to the method of the present invention may be tested directly or indirectly and may require some form of treatment prior to testing. For example, a blood sample or urine sample may require one or more separation steps prior to testing. Further, to the extent that the biological sample is not in liquid form, (for example it may be a solid, semi-solid or a dehydrated liquid sample) it may require the addition of a reagent, such as a buffer, to mobilize the sample.

As used herein, "subject" means a mammal, including, but not limited to, a human, horse, bovine, dog, or cat. The subject is whom it is desirable to assess the risk of cardio-vascular events, whether diabetic or not.

The term "determining the expression level of a gene/protein on a non protein basis" relates to methods which are not restricted to the secondary gene translation products, i.e proteins, but on other levels of the gene expression, like the mRNA, premRNA and genomic DNA structures.

By "array" or "matrix" an arrangement of addressable locations or "addresses" on a device is meant. The locations can be arranged in two dimensional arrays, three dimensional arrays, or other matrix formats. The number of locations can range from several to at least hundreds of thousands. Most importantly, each location represents a totally independent reaction site. Arrays include but are not limited to nucleic acid arrays, protein arrays and antibody arrays. A "nucleic acid array" refers to an array containing nucleic acid probes, such as oligonucleotides, nucleotide analogues, polynucleotides, polymers of nucleotide analogues, morpholinos or larger portions of genes. The nucleic acid and/or analogue on the array is preferably single stranded. Arrays wherein the probes are oligonucleotides are referred to as "oligonucleotide arrays" or "oligonucleotide chips." A "microarray," herein also refers to a "biochip" or "biological chip", an array of regions having a density of discrete regions of at least about $100/cm^2$, and preferably at least about $1000/cm^2$. The regions in a microarray have typical dimensions, e.g., diameters, in the range of between about 10-250 µm, and are separated from other regions in the array by about the same distance. A "protein array" refers to an array containing polypeptide probes or protein probes which can be in native form or denatured. An "antibody array" refers to an array containing antibodies which include but are not limited to monoclonal antibodies (e.g. from a mouse), chimeric antibodies, humanized antibodies or phage antibodies and single chain antibodies as well as fragments from antibodies.

The term "expression levels" refers, e.g., to a determined level of gene expression. The term "pattern of expression levels" refers to a determined level of gene expression compared either to a reference gene (e.g. housekeeper or inversely regulated genes) or to a computed average expression value (e.g. in DNA-chip analyses). A pattern is not limited to the comparison of two genes but is more related to multiple comparisons of genes to reference genes or samples. A certain "pattern of expression levels" may also result and be determined by comparison and measurement of several genes disclosed hereafter and display the relative abundance of these transcripts to each other.

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy or diseased individuals, serving as a reference group.

"Biological activity" or "bioactivity" or "activity" or "biological function", which are used interchangeably, herein mean an effector or antigenic function that is directly or indirectly exerted by a polypeptide (whether in its native or denatured conformation), or by any fragment thereof in vivo or in vitro. Biological activities include but are not limited to binding to polypeptides, binding to other proteins or molecules, enzymatic activity, signal transduction, activity as a DNA binding protein, as a transcription regulator, ability to bind damaged DNA, etc. A bioactivity can be modulated by directly affecting the subject polypeptide. Alternatively, a bioactivity can be altered by modulating the level of the polypeptide, such as by modulating expression of the corresponding gene.

The term "hybridization based method", as used herein, refers to methods imparting a process of combining complementary, single-stranded nucleic acids or nucleotide analogues into a single double stranded molecule. Nucleotides or nucleotide analogues will bind to their complement under normal conditions, so two perfectly complementary strands will bind to each other readily. In bioanalytics, very often labeled, single stranded probes are in order to find complementary target sequences. If such sequences exist in the sample, the probes will hybridize to said sequences which can then be detected due to the label. Other hybridization based methods comprise microarray and/or biochip methods. Therein, probes are immobilized on a solid phase, which is then exposed to a sample. If complementary nucleic acids exist in the sample, these will hybridize to the probes and can thus be detected. These approaches are also known as "array based methods". Yet another hybridization based method is PCR, which is described below. When it comes to the determination of expression levels, hybridization based methods may for example be used to determine the amount of mRNA for a given gene.

The term "a PCR based method" as used herein refers to methods comprising a polymerase chain reaction (PCR). This is a method of exponentially amplifying nucleic acids, e.g. DNA by enzymatic replication in vitro. As PCR is an in vitro technique, it can be performed without restrictions on the form of DNA, and it can be extensively modified to perform a wide array of genetic manipulations. When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR).

Moreover, PCR-based methods comprise e.g. real time PCR, and, particularly suited for the analysis of expression levels, kinetic or quantitative PCR (qPCR).

The term "Quantitative real-time PCR" (qPCR)" refers to any type of a PCR method which allows the quantification of the template in a sample. Quantitative real-time PCR comprise different techniques of performance or product detection as for example the TaqMan technique or the LightCycler technique. The TaqMan technique, for examples, uses a dual-labelled fluorogenic probe. The TaqMan real-time PCR measures accumulation of a product via the fluorophore during the exponential stages of the PCR, rather than at the end point as in conventional PCR. The exponential increase of the product is used to determine the threshold cycle, CT, i.e. the number of PCR cycles at which a significant exponential increase in fluorescence is detected, and which is directly correlated with the number of copies of DNA template present in the reaction. The set up of the reaction is very similar to a conventional PCR, but is carried out in a real-time thermal cycler that allows measurement of fluorescent molecules in the PCR tubes. Different from regular PCR, in TaqMan real-time PCR a probe is added to the reaction, i.e., a single-stranded oligonucleotide complementary to a segment of 20-60 nucleotides within the DNA template and located between the two primers. A fluorescent reporter or fluorophore (e.g., 6-carboxyfluorescein, acronym: FAM, or tetrachlorofluorescin, acronym: TET) and quencher (e.g., tetramethylrhodamine, acronym: TAMRA, of dihydrocyclopyrroloindole tripeptide "minor groove binder", acronym: MGB) are covalently attached to the 5' and 3' ends of the probe, respectively. The close proximity between fluorophore and quencher attached to the probe inhibits fluorescence from the fluorophore. During PCR, as DNA synthesis commences, the 5' to 3' exonuclease activity of the Taq polymerase degrades that proportion of the probe that has annealed to the template (Hence its name: Taq polymerase+PacMan). Degradation of the probe releases the fluorophore from it and breaks the close proximity to the quencher, thus relieving the quenching effect and allowing fluorescence of the fluorophore. Hence, fluorescence detected in the realtime PCR thermal cycler is directly proportional to the fluorophore released and the amount of DNA template present in the PCR.

The term "determining the protein level", as used herein, refers to methods which allow the quantitative and/or qualitative determination of one or more proteins in a sample. These methods include, among others, protein purification, including ultracentrifugation, precipitation and chromatography, as well as protein analysis and determination, including the use protein microarrays, two-hybrid screening, blotting methods including western blot, one- and two dimensional gelelectrophoresis, isoelectric focusing as well as methods being based mass spectrometry like MALDI-TOF and the like.

"Primer pairs" and "probes", within the meaning of the invention, shall have the ordinary meaning of this term which is well known to the person skilled in the art of molecular biology. In a preferred embodiment of the invention "primer pairs" and "probes", shall be understood as being polynucleotide molecules having a sequence identical, complementary, homologous, or homologous to the complement of regions of a target polynucleotide which is to be detected or quantified. In yet another embodiment nucleotide analogues and/or morpholinos are also comprised for usage as primers and/or probes.

The term "Cardiovascular Disease" (CVD) is generally defined as Acute Coronary Syndrome, stroke, or overt manifestation of peripheral arterial disease.

The term "statistically significant" or "statistical significance" means that there is the low probability of obtaining at least as extreme results given that the null hypothesis is true. Statistical significance helps to decide if a subject or patient is at risk of developing cardiovascular disease by the measurement of the increase of at least one gene of interest. In any experiment or observation that involves drawing a sample from a population, there is always the possibility that an observed effect would have occurred due to sampling error alone. But if the probability of obtaining at least as extreme result (large difference between two or more sample means), given the null hypothesis is true, is less than a pre-determined threshold (e.g. 5% chance), then one can conclude that the observed effect actually reflects the characteristics of the population rather than just sampling error. P-values are often coupled to a significance or alpha (a) level, which is also set ahead of time, usually at 0.05 (5%). Thus, if a p-value is found to be less than 0.05, then the result would be considered statistically significant and the null hypothesis would be rejected. Other significance levels, such as 0.1 or 0.01, are also used, depending on various factors.

The "coefficient of determination" is a number that indicates how well data fit a statistical model and is represented by $r^2$. An $r^2$ of 1 indicates that the regression line perfectly fits the data and there is a high correlation.

Generally speaking, the invention is a method performed on a biological sample of a patient or subject at risk of developing Cardiovascular Disease (CVD). There is a strong relationship between the excretion of albumin in the urine and the risk of CVD, whereby increasing excretion of albumin is strongly predictive of CVD. The method identifies an earlier biologic event that diagnoses the risk of CVD several years before an increase in albumin excretion is evident. The measurement of urinary mRNA for proteins found in renal cells (glomerular epithelial cells or "podocytes"), the injury and loss of which is the reason why albumin is filtered at higher rates in these individuals, provides a more powerful and earlier means of identifying risk for CVD in individual patients.

The method for predicting the risk of cardiovascular disease of a subject at risk of developing cardiovascular disease comprises: obtaining a biological sample from the subject; determining the expression level of at least one gene of interest, wherein the at least gene of interest is selected from the group consisting of nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin; comparing the expression levels of the at least one gene of interest at first time period and a second time period; and predicting the likelihood of cardiovascular disease developing in the subject based on the outcome of the comparison of the expression levels of the at least gene of interest at different time periods.

Any increase in expression of the at least one gene of interest from a first time period may predict the likelihood of a cardiovascular disease occurring at second time period. The second time period may be between at least about 1 year to about 10 years from the first time period. Preferably, the second time period is between about 2 years and 8 years from the first time period; alternatively, between about 3 and 6 years from the first time period. A third time period may be used to measure the expression of at least one gene of interest. The third time period may be between at least 1 year to about 10 years from the second time period. Preferably, the third time period is between about 2 years and 8 years from the second time period; alternatively, between about 3 and 6 years from the second time period. In another embodiment, a fourth time period may be used to measure the expression of the at least gene of interest. The fourth time period may be between at least 1 year to about 10 years from the third time period. Preferably, the fourth time period is between about 2 years and 8 years from the third time period; alternatively, between about 3 and 6 years from the third time period. Additional time periods may be deployed in a similar fashion if the subject has not been diagnosed or predicted to be at risk for cardiovascular disease. Once a baseline is established from the initial increase of the at least gene of interest, then the prediction or prognosis of cardiovascular disease may be implemented.

In one embodiment, a baseline may be established that is at least between 0.2 million to 2 million copies of the at least one gene of interest, such that any statistical significant increase from about 0.2 to 2 million copies as measured during the first time period may indicate a subject to be at risk for developing cardiovascular disease. Measurement of the AER and eGFR may also establish a baseline.

The increase of the at least one gene of interest from the first time period to the second time period must be statistically significant, i.e. with a p-value less than 0.05, alternatively, a p-value less than 0.01, alternatively a p-value less than 0.1, alternatively a p-value less than 0.05. In one embodiment, the increase of the at least gene of interest from the first time period to the second time period may be between about 1-5 million copies, alternatively between about 2-4 million copies, alternatively between 3-4 million copies. In one embodiment, the increase of the at least one gene of interest from the second time period to the third time period.

In one embodiment, at least two genes of interest may correlate with the increase from the first time period to the second time period, or from the second time period to the third time period. A high degree of correlation may include a coefficient of determination to be $r^2$ of at least between 0.5 to about 0.9.

The significance of this invention is that it provides health care workers with a very early (preclinical) biomarker which will result in more effective interventions to prevent CVD. The method may be performed in Type II diabetic patients or in patients that are not diabetic.

The diagnosis may be conducted by measurement of other podocyte-associated proteins or their mRNAs for the purpose of predicting cardiovascular risk, including: nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin. In one embodiment, the measurement is taken from a urinary sample from the subject or patient. Alternatively, the sample may be taken from any fluid from the subject or patient.

Any method of measuring urinary protein or mRNA levels of nephrin, podocin, synaptopodin, Wilm's Tumor-1 (WT-1), UCH-L1, pax-8, RAP1GAP, Rap1a, RAP1b, beta-1 integron, CD2-Associated Protein (CD2AP), NEPH-1, ZO-1, alpha-actinin 4, Lmx-1b, Pod-1, podocalyxin, podoendin, FAT, and p-cadherin, as a means to predict cardiovascular risk.

According to the invention, at least one substance can be used for detecting the expression and/or function of urinary protein or mRNA levels of nephrin, podocin, synaptopodin, Wilm's Tumor-1 (WT-1), UCH-L1, pax-8, RAP1GAP, Rap1a, RAP1b, beta-1 integron, CD2-Associated Protein (CD2AP), NEPH-1, ZO-1, alpha-actinin 4, Lmx-1b, Pod-1, podocalyxin, podoendin, FAT, and p-cadherin. This also makes it possible to provide a diagnosis, prognosis, or to predict diseases which are connected with CVD. For example, an antibody which is directed against nephrin, podocin, synaptopodin, Wilm's Tumor-1 (WT-1), UCH-L1, pax-8, RAP1GAP, Rap1a, RAP1b, beta-1 integron, CD2-Associated Protein (CD2AP), NEPH-1, ZO-1, alpha-actinin 4, Lmx-1b, Pod-1, podocalyxin, podoendin, FAT, and p-cadherin may be employed in a detection method, such as ELISA (enzyme-linked-immuno sorbent assay), a dot blotting method, latex aggultuination-turbidimetric immunoassay (LA), or immunochromatography. Other substances that may be used for the diagnostic detection are oligonucleotides, which are suitable, for example, using the polymerase chain reaction (PCR), for detection of mature mRNA and/or pre-mRNA, either with or without amplification of the RNA or cDNA to be analyzed. Yet other substances that may be used for the diagnostic detection are polypeptides, including antibodies, which are suitable for detection of nephrin, podocin, synaptopodin, Wilm's Tumor-1 (WT-1), UCH-L1, pax-8, RAP1GAP, Rap1a, RAP1b, beta-1 integron, CD2-Associated Protein (CD2AP), NEPH-1, ZO-1, alpha-actinin 4, Lmx-1b, Pod-1, podocalyxin, podoendin, FAT, and p-cadherin activity or activation, or production of protein (e.g., by ELISA or Western Blot).

Any probes to the at least one gene of interest may be a fragment of the nucleic acid molecule, which is intended to indicate the probe is a nucleic acid comprising a subset of a nucleic acid molecule according to one of the claimed sequences. The prove may be a variant of the nucleic acid molecule of the at least gene of interest, which is substantially similar in structure and biological activity to a nucleic acid molecule according to one of the claimed sequences of the at least gene of interest. The probe may be a homologue of the nucleic acid molecule of the at least gene of interest, which has one or more nucleotides added, deleted, substituted or otherwise chemically modified in comparison to a nucleic acid molecule according to one of the claimed sequences of the at least gene of interest, provided always that the homologue retains substantially the same binding properties as the latter. The probe may be a "derivative of the at least one gene of interest, which refers to a nucleic acid molecule that has similar binding characteristics to a target nucleic acid sequence as a nucleic acid molecule according to one of the claimed sequences of the at least gene of interest. Alternatively, the probe may have a sequence identity of at least X %, which refers to a sequence identity as determined after a sequence alignment of the at least one gene of interest carried out with the family of BLAST algorithms as accessible on the respective Internet domain provided by NCBI.

The invention also relates to a diagnostic kit. This kit comprises at least one substance which is suitable for detecting the expression and/or function of protein or mRNA levels of nephrin, podocin, synaptopodin, Wilm's Tumor-1 (WT-1), UCH-L1, pax-8, RAP1GAP, Rap1a, RAP1b, beta-1 integron, CD2-Associated Protein (CD2AP), NEPH-1, ZO-1, alpha-actinin 4, Lmx-1b, Pod-1, podocalyxin, podoendin, FAT, and p-cadherin, for the purpose of diagnosing, prognosing, or predicting diseases which are connected to CVD. The diagnostic kit according to the invention comprising a substance for detecting the expression and/or function of nephrin, podocin, synaptopodin, Wilm's Tumor-1 (WT-1), UCH-L1, pax-8, RAP1GAP, Rap1a, RAP1b, beta-1 integron, CD2-Associated Protein (CD2AP), NEPH-1, ZO-1, alpha-actinin 4, Lmx-1b, Pod-1, podocalyxin, podoendin, FAT, and p-cadherin, additional assay components (e.g., reagents), labels, and/or instructions.

The invention is superior to currently employed methodologies for identifying cardiovascular risk, because the method of prediction and prognosis targets the specific consequence of endothelial/podocyte cell injury by measuring podocyte cell shedding in the urine rather than albumin excretion rates. The method of prediction and prognosis is superior because the method of prediction and prognosis targets more specifically an early event in vascular injury and because the method of prediction and prognosis does so several years before the currently employed method of measuring urinary albumin excretion.

Recognizing that urinary albumin excretion rate is determined not only by podocyte injury and increased filtration, but also by the proportion of filtered albumin taken up by the proximal tubule, early glomerular (and presumably systemic) endothelial injury is detected as an increase in urinary podocyte shedding (podocyturia) rather than the onset of progressive albuminuria. Podocyturia is more relevant and earlier biomarker of endothelial injury than moderate albuminuria (previously microalbuminuria). Diabetic individuals who presented initially with "normoalbuminuria" (<20 mcg/mg albumin/creatinine excretion rates) are tested, and examined whether differences in podocyte shedding rates among these individuals could identify those who would subsequently develop adverse cardiovascular outcomes (acute coronary syndrome, ACS, stroke, peripheral vascular disease, PVD) when followed for seven years.

Hereinafter, the present invention is more specifically described by way of examples; however, the present invention is by no means limited thereto, and various applications are possible without departing from the technical idea of the present invention.

Example 1

Methods:
Study Design:
This is a clinical cohort follow-up study in a retrospective patient series participating in a longitudinal biologic sample repository, with additional biomarker measurements.
Population:
Enrolled patients were either outpatients or in-patients with Type II diabetes mellitus seen for initial presentation and then followed for almost 10 years, as well as twenty healthy controls from whom urine was collected for measurement of biomarkers (see below). Consent was secured from study subjects to use their left over urine samples and to review their medical charts for blood/urine test results and for all relevant clinical diagnoses. This study was approved by institutional research board (IRB).

106 diagnosed type 2 diabetic patients were identified (age: 25-89 years; men/women: 46/60) on whom follow up visits (clinical data and urine samples) were available and complete for seven years since their initial visit, whose urinary albumin excretion rates on Visit 1 were below what was traditionally termed "microalbuminuria" (<20 mcg/mg albumin/creatinine), and who had no history of cardiovascular diseases of any kind, in particular ACS, stroke or PVD. Since patients were pre-selected to have survived for 7 years since Visit 1, mortality due to any cause was excluded from the composite outcome. Hypertension (present in 17 patients on Visit 1) was not considered an adverse CV outcome.

Sample Collection

Urine and blood samples were collected during Visit 1 along with a complete medical history and physical examination. Subjects were generally seen at 6 months intervals. Follow-up visits were reviewed for approximately 7 years after Visit 1 to obtain interval history, physical examination, and blood and urine test results at each visit. Clinical data, including new onset CVD, as well as urine and blood samples were analyzed from Visit 1, Visit 2 (mean follow up after Visit 1 of 3.8 years; SD 0.6 years) and Visit 3 (mean follow up after Visit 2 of 3.2+/−0.7 years). All Urine and plasma samples were stored at −80° C. till RNA extraction. Urine samples were analyzed for albumin excretion rates (AER) (as mcg/mg creatinine) and for podocin and nephrin mRNA levels (see below). All samples were assigned a study number that linked them to the clinical information in clinical charts. Samples were coded and analyzed with the lab operator blinded to the visit number, the subject it belonged to, or whether this subject eventually developed CVD or not.

Procedures
Volume of Urine for Assay:
An assumption was made that the samples contain low mRNA levels. Podocin and nephrin mRNA were not detectable in 25 to 30% of samples starting with <1 ml of urine. Therefore, 1.7 ml were used in all assays.

Urine Processing:
Urine was centrifuged at 4° C. for 15 minutes at 4000 rpm (3200 g) on a table-top centrifuge. The low-speed centrifugation conditions used do not pellet exosomes and other subcellular structures, so an assumption was made that the urine pellet mRNAs measured are derived from whole cells and are therefore a measure of the podocyte detachment rate. The supernatant was removed and stored at −20° C. for protein, creatinine, and other measurements. The urine pellet was suspended in 1.5 ml of cold diethylpyrocarbonate-treated PBS (pH, 7.4) at 4° C. The pellet material in 1.5 ml PBS was then centrifuged at 12,000 rpm in a mini-centrifuge for 5 minutes at 4° C. The supernatant was discarded. 350 µl of RLT buffer was added to the washed pellet, containing β-mercaptoethanol at 10 µl/ml of RLT buffer, according to the manufacturer protocol (RNeasy kit; Qiagen—Germantown, Md.). The pellet was suspended in RLT/β-mercaptoethanol buffer and then frozen at −80° C. for assay.

RNA Preparation and Quantitative RT-PCR Assay:
The total urine pellet RNA was isolated using the manufacturer protocol (RNeasy Mini Kit; Qiagen—Germantown, Md.). Quantitation of the absolute nephrin and podocin, mRNA abundance was performed using the CFX96

Touch™ Real-Time PCR Detection System (Bio-rad, USA) using TaqMan probes, with sample cDNA in a final volume of 25 μl per reaction. TaqMan Probes (BIO-RAD Laboratories, USA) used were as follows: human nephrin (NPHS1: NM 004646.3) and podocin (NPHS2: NM_014625.2). All data were from 2-μl sample measured in duplicate. Standard curves were constructed for each assay using serially diluted cDNA standards. Assays were accepted only if the $r^2$ was >0.97 for standard curves. Human nephrin and podocin cDNA of known sequence and concentration were used as standards for each assay so that the data could be calculated on number of copy basis for each probe. RNA urine analysis quality, recovery, and stability were performed.

Stability of Urine mRNAs and Sample Handling:

Urine mRNA markers decay over 4-6 hours after voiding if not stored properly; decay occurs more quickly if the urine is stored at room temperature. However, urine mRNA markers remain stable if properly stored at −80° C. as compared to 4° C. or room temperature. At −80° C. mRNA markers remain remarkably constant for prolonged periods of time. For this study, the collected urine samples had all been stored at −80° C.

Statistical Analysis:

Continuous variables are summarized as mean±standard deviation or median (inter-quartile range) as applicable. Categorical variables were summarized as counts and percentages. Study subjects were grouped into tercile groups based on their baseline (Visit 1) AER, nephrin, and podocin mRNA levels (low, intermediate and high). Baseline characteristics were compared among the three groups. The primary outcome of interest was the time for diagnosis of CVD, which included documentation of any of the following during the period of follow up for each patient: coronary artery disease, myocardial infarction, heart failure, cerebrovascular accident (stroke) and PVD. Time-to-Event (CVD diagnosis) analysis was performed via Product-Limit or Kaplan-Meier estimates which were compared across the 3 terciles. Cox regression was used to adjust for confounders (SPSS 21; IBM, NY). Rate of rise in nephrin and podocin urinary mRNA, as well as albuminuria levels was compared across study groups via repeated measures of analysis of variance analysis (RM-ANOVA). A p value less than 0.05 was used to indicate statistical significance.

III. Results

Figure 1:
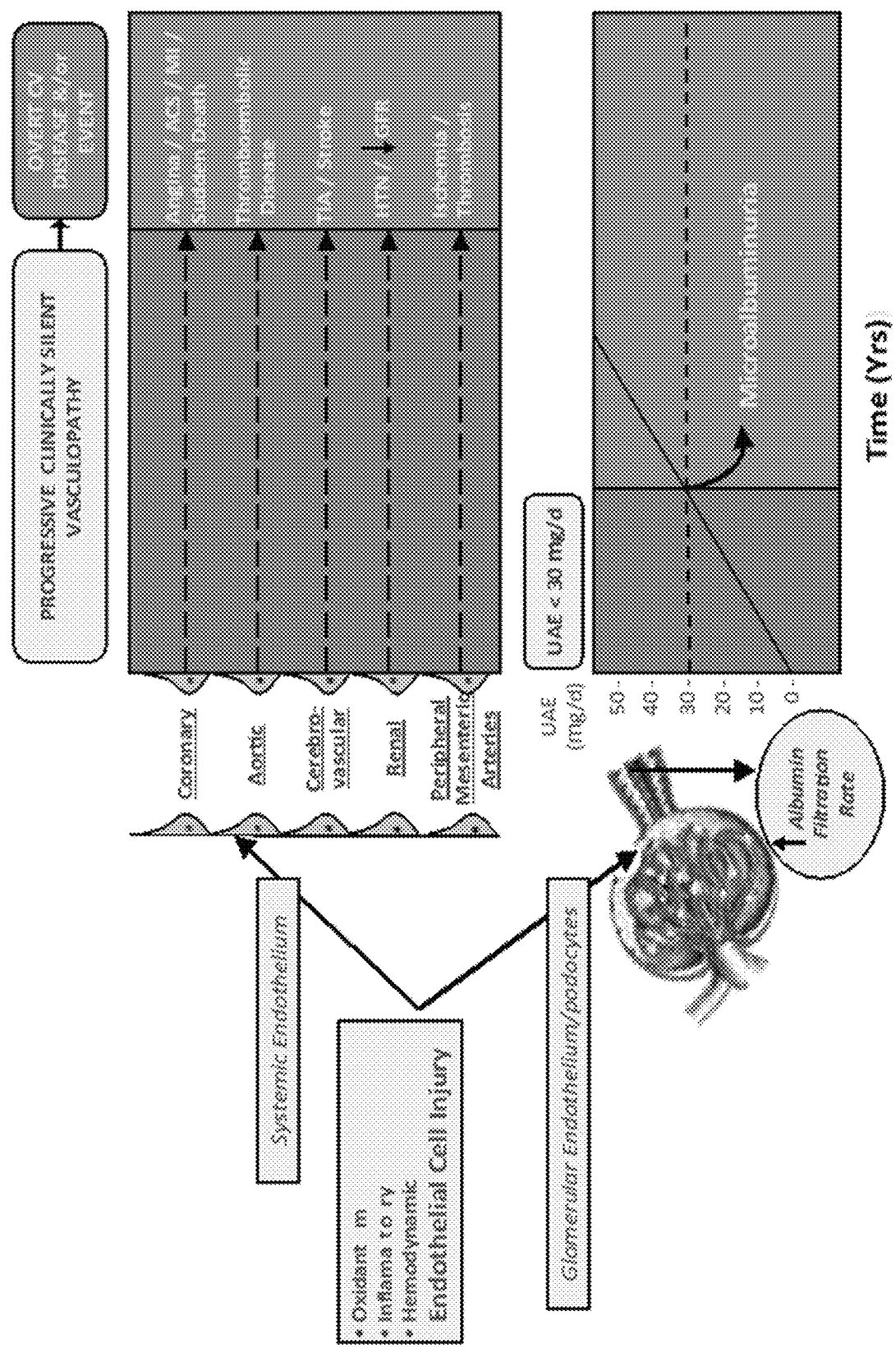
FIG. 1 is a flow chart of the comparative pathophysiology and clinical consequences of endothelial cell injury in systemic versus renal circulations. The high hydraulic permeability, large surface area, and elevated capillary hydraulic pressure in glomerular endothelium amplifies the functional consequence (increased albumin filtration) of early endothelial injury. The emergence of "microalbuminuria" thus unmasks systemic endothelial injury occurring simultaneously in other beds and progressing silently to disease expression years later.
Figure 3A:
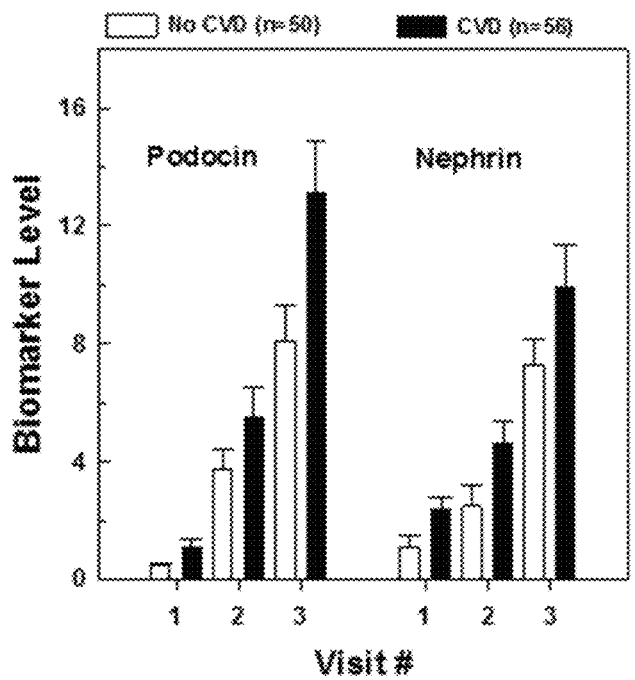
FIGS. 3A-3B are graphs of Progression of the increases in podocyturia markers and the corresponding decline in estimated Glomerular Filtration Rate (eGFR) in CVD (black bars) versus No-CVD (open bars) over the seven year follow-up period.
Figure 3B:
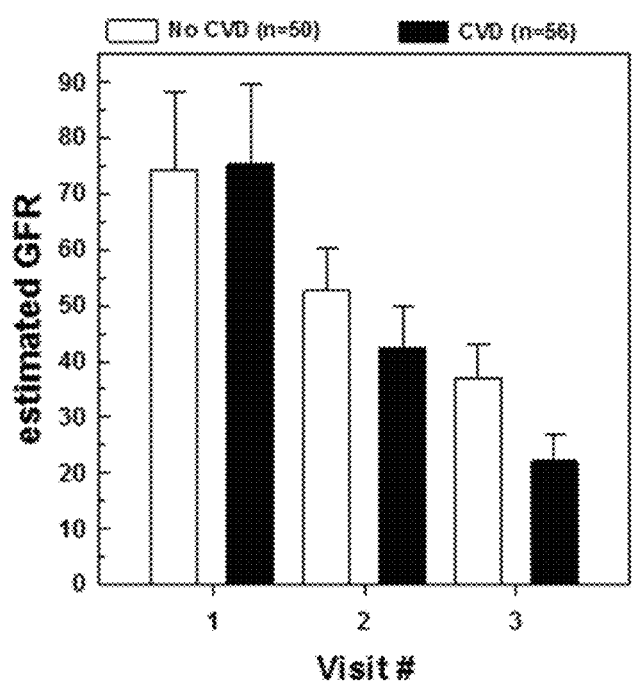

All Patients:

FIG. 2A summarizes the change of three urinary biomarkers (podocin mRNA, nephrin mRNA, albumin) sampled at three visits (1, 2 and 3) that spanned a median follow-up period of 7.1 years. Briefly, at Visit 1, all 106 subjects in this diabetic study population were free of any known cardiovascular disease and had "normal" albuminuria levels [AER <20 mcg/mg; median (IQR)=9.5 (6.5-10.5)]. All three urine biomarkers increased over time in all patients, consistent with progression of diabetic vascular injury. At Visit 2 (3 to 4 years later), AER had increased substantially [195 (90-166); P<0.001] and this was followed with an additional marked increase after 6 to 8 years at visit 3 [866 (679-965); P<0.001], as shown in FIG. 2A. The corresponding urinary podocin mRNA [0.65 (0.4-1.1), 4.3 (3.8-5.8) and 10.2 (8.6-12.2) million copies], and nephrin mRNA [1.8 (1.1-2.5), 3.7 (2.3-4.8) and 8.3 (7.3-10.3) million copies] levels also increased progressively between Visits 1 and 3 (all P<0.001). Additional evidence of vascular and renal injury in all patients is the progressive decline in eGFR, albeit greater in those who sustained a CV event during the seven years of follow up, as shown in FIGS. 3A-3B.

Cardiovascular Disease Sub-Cohorts:

Urinary biomarker levels in all patients were also analyzed separately for the subject sub-cohorts of those who developed ("CVD") versus did not develop ("No-CVD") cardiovascular events during the seven-year follow-up period between Visits 1 and 3 (FIG. 2A). Mean baseline (Visit 1) levels of both podocin mRNA (0.45±0.12 vs. 1.07±0.31; P<0.001) and nephrin mRNA (1.10±0.36 vs. 2.36±0.44; P<0.001) were significantly greater in subjects who developed CVD during follow-up, whereas AER at baseline was similar between the No-CVD and CVD subgroups (8.5±2.2 vs. 9.1±2.3; not significant). Comparison of the rate of increase in biomarkers from Visit 1 to Visit 2, and from Visit 2 to Visit 3 revealed a clearly increased rate of rise in CVD versus No CVD patients (FIG. 2A). FIGS. 2B and 2C summarize all clinical and biomarker data for CVD and No-CVD patients at baseline and during the subsequent two visits.

Of note, nephrin and podocin mRNA levels in diabetic No-CVD patients at Visit 1, while significantly less than those with CVD, were nevertheless greater than mean values obtained in 20 normal age-matched volunteers (0.2±0.06 and 0.1±0.02 million copies, respectively.

Figure 4C:
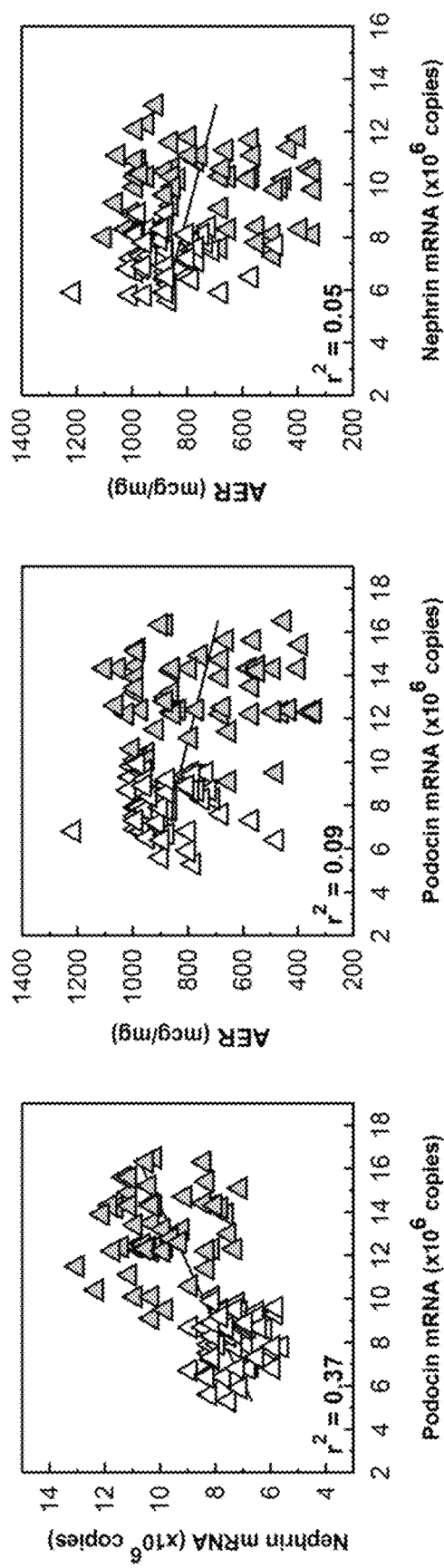

Correlations Among Urinary Biomarkers and Relation to Cardiovascular Disease:

Baseline or Visit 1 levels of urinary nephrin and podocin mRNA levels were highly correlated ($r^2$=0.63), but neither was well correlated to the baseline albuminuria levels ($r^2$=0.15 and 0.09 for podocin and nephrin, respectively) (FIG. 4A). The increases in podocin and nephrin mRNA longitudinally over time appeared to track each other fairly closely and remained well correlated despite the substantial rise in absolute levels ($r^2$=0.40 and 0.37 at visits 2 and 3, respectively) (FIG. 4B-4C, Middle/Bottom). Interestingly, the progression from normal to moderate albuminuria observed between visits 1 and 2 appears to track with the change in both podocin ($r^2$=0.41) and nephrin ($r^2$=0.37). More importantly, nephrin and podocin mRNA levels were distinctly higher in CVD patients at all visits including at baseline. This characteristic of urinary podocin and nephrin was however not true for AER which did not discriminate between CVD and No CVD at baseline. AER was significantly increased for the CVD sub-cohort compared to No-CVD counterparts at Visit 2, but this separation was no longer true at Visit 3.

Time to Cardiovascular Event Analysis:

To ascertain the early discriminatory power of each of the urinary biomarkers in predicting CVD, subjects were primarily sub-categorized to 3 groups based on their Visit 1 levels using specific cutoff values for AER (<7 (Low); 7-10 (med) and >10 mcg/mg) or using tercile groups in the case of podocin and nephrin mRNA. Comparisons of subject characteristics, clinical data and laboratory values for these tercile groups are detailed in FIG. 5. Development of cardiovascular disease after enrollment was then investigated as a Time-to-Event analysis comparing the derived subgroups for each of the three biomarkers. This analysis indicated that, low, medium and high levels of AER at baseline, albeit all within normal levels (<20 mcg/mg), do not separate patients who developed versus those who did not develop CVD within the 7 year follow-up period, as shown in FIG. 6A; and FIG. 5B with p=0.127. This was in sharp contrast with the results obtained with either podocin or nephrin mRNA levels, as shown in FIGS. 6B-6C, respectively, or FIG. 5B. In the latter cases, increasing levels of podocin and nephrin levels at baseline were highly significantly (both P<0.001) predictive of development of CVD, as was the relative time to CVD diagnosis or event occurrence. To complement this analysis, biomarker levels as continuous variables were considered, and the associated covariate-adjusted hazard ratios by multivariate Cox Regression were highest in case of podocin mRNA [HR=15.9 (6.1-41.8); p<0.001], intermediate for nephrin mRNA [HR=7.61 (3.75-15.5); p<0.001] and lowest for AER [HR=1.17 (1.01-1.36); p=0.041], as shown in FIG. 5B.

IV. Discussion

All Patients:

Our study population consisted of relatively young (mean age 47 years) diabetics who, despite being "normoalbuminuric", carried other risk factors for CVD including a high proportion of smokers and overweight/obese individuals and relatively poor glycemic control, as shown in FIG. 2C and FIG. 2B. Not surprisingly, there was evidence of progressive vascular injury in all patients manifesting as progressive increases in all three urinary biomarkers (AER and nephron/podocin mRNA).

Cardiovascular Disease Sub-Cohorts:

Despite similar clinical characteristics and normal AER at initial presentation, however, about half the patients developed an over CV event over the subsequent seven years. The rate of increase in biomarkers was accelerated in CVD versus No-CVD patients, supporting the notion that podocyte injury and albuminuria are indeed a reflection of endothelial/vascular injury occurring silently and simultaneously in the cerebral, coronary, and systemic circulations.

Correlations Among Urinary Biomarkers and Relation to Cardiovascular Disease:

The data summarized in FIG. 6A-6C provides evidence for the superiority of nephrin/podocin mRNA over AER as a faithful indicator of CV injury over time. Nephrin and podocin mRNA levels correlated well with each other, even as injury progressed over seven years, suggesting that podocyte shedding is indeed well reflected by both measurements. More importantly, at all three visits, CVD patients had distinctly higher values of urinary podocin/nephrin mRNA than their No-CVD counterparts. That AER at Visit 1 did not correlate with nephrin or podocin mRNA nor did it distinguish between CVD and No-CVD patients supports strongly the notion that the major determinant of AER in this early stage of injury is not filtered albumin, but the fraction of it retrieved in the proximal tubule, as suggested by others. At visit 2, AER has increased to levels within the moderate albuminuria range (previously termed "microalbuminuria") and indeed at this stage of injury, at which time filtered albumin contributes increasingly to the final value of AER, the well—established capacity of moderate albuminuria to distinguish CVD form No-CVD is evident and AER correlates well with both nephrin and podocin mRNA levels. By Visit 3, however, AER had increased to the macroalbuminuric range and is no longer relevant to identifying CV risk. Even at Visit 3, however, urinary podocin/nephrin mRNAs continues to distinguish the two patient groups (Bottom Panel of FIG. 4C).

Time to Cardiovascular Event Analysis: FIG. 2's Remarkable Predictive Power of Podocyturia to Identify Patients Destined to Develop CVD Under physiologic ("normal") conditions, an appreciable amount of albumin is filtered across glomerular epithelial cells (podocytes). In healthy children and adults, the amount of albumin appearing in the urine is the algebraic difference between filtered albumin and the amount retrieved by the S1 segment of the proximal tubule. An increasingly large body of evidence in humans and other mammals assigns a larger role for proximal tubule albumin retrieval in determining urinary albumin excretion than previously appreciated. Studies have established that proximal tubule albumin retrieval rates are highly regulated and are also influenced by total proximal tubule mass and disease states, including diabetes. It therefore seems reasonable to assume that individuals vary widely in the proximal handling of filtered loads of albumin and fractional albumin retrieval. The tight coupling between AER and CV outcomes, however, suggests strongly that it is progressive glomerular (and systemic) vascular injury, leading to an increase in filtered albumin that underlies progressive albuminuria in these individuals. Given the above-cited considerations regarding normal handling of filtered albumin by the proximal tubule, for urinary albumin to reflect mainly filtered albumin, proximal tubule retrieval of albumin must be saturated. Only then would vascular injury (filtered albumin) correlate so strongly with urinary albumin, as was demonstrated in numerous large population studies. In an individual patient, however, the time elapsing between the onset of vascular injury and the saturation of proximal retrieval cannot be known; increased filtration of albumin may be present for years before urinary albumin levels begin to rise.

The present studies addressed this hypothesis by targeting an earlier event in the vascular injury pathway, podocyte shedding, and assessing the capacity of podocyturia to predict CV outcomes before AER increases above the "normal" range. Podocyturia correlates strongly with proteinuria and renal functional deterioration in diabetic and non-diabetic individuals, as well as in patients with inflammatory and non-inflammatory glomerular diseases, but it has not been previously evaluated as an early predictor of systemic vascular injury. The rate of urinary podocyte shedding is best measured by real-time PCR quantitation of mRNA for unique podocyte-specific proteins (such as nephrin, podocalyxin, podocin, synaptopodin, and others).

Despite the relatively small number of patients with Type II diabetes who had normoalbuminuria in our cohort, forward analysis of the power of urinary podocyte shedding to predict CV outcomes was remarkable. The accelerated pace of vascular injury in diabetics provided an ideal population in which the validity of this measurement could be demonstrated over a relatively short follow-up period, but the usefulness of podocyturia in predicting CV events likely extends to non-diabetic subjects as well. It is important to note that the study population is composed of relatively young individuals (mean age 47 years) who had normal AER and whose duration of diabetes was a mean of 6.3±1.5 years, as shown in FIG. 2B.

In conclusion, the disclosed examples highlight the usefulness of urinary podocyte mRNA quantitation as a tool for assessment of on-going vascular injury, and its capacity to identify those destined to develop moderate albuminuria and CVD several years before either of these outcomes is detectable by present methodologies. The capacity of the mass of glomerular endothelial cells to sense, amplify, and "report" (through podocyturia) on the health of the systemic endothelium assigns a novel role for the renal glomerulus as an endogenous "endotheliometer", providing crucial real-time information on the presence, extent and progression of systemic vascular injury.

Prophetic Example 1

The blood or any fluid from a subject may be tested for the mRNA levels of nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin. The total pellet RNA is isolated using the manufacturer protocol (RNeasy Mini Kit; Qiagen—Germantown, Md.). Quantitation of the absolute nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin, mRNA abundance is performed using the CFX96 Touch™ Real-Time PCR Detection System (Bio-rad, USA) using TaqMan Fast Universal PCR Master Mix, with sample cDNA in a final volume of 25 µl per reaction. TaqMan Probes (Applied Biosystems) used were as follows: human NPHS1 (nephrin gene accession number: Q1KMS5) and NPHS2 (podocin gene accession number: Q9NP85). All data are from 2-µl sample measured in duplicate. Standard curves are constructed for each assay using serially diluted cDNA standards. Assays are accepted only if the $r^2$ was >0.97 for standard curves. Human nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin cDNA of known sequence and concentration are used as standards for each assay so that the data could be calculated on number of copy basis for each probe. RNA fluid analysis quality, recovery, and stability is performed.

Continuous variables are summarized as mean±standard deviation or median (inter-quartile range) as applicable. Categorical variables are summarized as counts and percentages. Study subjects are grouped into tercile groups based on their baseline (Visit 1) AER, nephrin, and podocin mRNA levels (low, intermediate and high). Baseline characteristics are compared among the three groups. The primary outcome of interest is the time for diagnosis of CVD, which included documentation of any of the following during the period of follow up for each patient: coronary artery disease, myocardial infarction, heart failure, cerebrovascular accident (stroke) and PVD. Time-to-Event (CVD diagnosis) analysis is performed via Product-Limit or Kaplan-Meier estimates which are compared across the 3 terciles. Cox regression is used to adjust for confounders (SPSS 21; IBM, NY). Rate of rise in nephrin and podocin urinary mRNA, as well as albuminuria levels is compared across study groups via repeated measures of analysis of variance analysis (RM-ANOVA). A p value less than 0.05 is used to indicate statistical significance.

The subjects should be free of any known cardiovascular disease during the first measurement of Human nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin. Any increase in the second measurement of Human nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin that is statistically significant P<0.05 will indicate that the subject is a risk for developing cardiovascular disease.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A method for predicting the risk of cardiovascular disease comprises:
   obtaining a first urine sample from a diabetic patient, at a first time period;
   determining the expression levels of nephrin and podocin; and measuring the levels of albumin in the first urine sample;
   comparing the expression levels of nephrin and podocin at the first time period to a baseline expression level of nephrin and podocin of and an increase of at least between 0.2 and 2 million mRNA copies/ml as measured during the first time period for an increased risk for cardiovascular disease, wherein the first time period is before the onset of any cardiovascular disease event and the cardiovascular disease event is defined as an albumin excretion greater than 20 mcg/mg of creatinine measured in the first biological sample; and
   predicting the risk of a cardiovascular disease event in the diabetic patient based on the outcome of the comparison of the expression levels of nephrin and podocin at different time periods and before an increase of 20 mcg/mg of creatinine in albumin excretion is detected, and wherein the increased expression of nephrin and podocin to at least 0.2 million copies/ml above the baseline, and wherein the cardiovascular disease event is selected from the group consisting of coronary artery disease, myocardial infarction, heart failure, cerebrovascular accident (stroke) and Peripheral vascular disease (PVD).

2. The method of claim 1, wherein comparing step further comprises comparing the increase in expression of nephrin and podocin from the first time period to the baseline that is statistically significant.

3. The method of claim 2, wherein the comparing step further comprises comparing the increase in expression of nephrin and podocin from the first time period to a second time period that is between 1 year to 10 years from the first time period.

4. The method of claim 3, further comprising comparing nephrin and podocin from the second time period to a third time period.

5. The method of claim 4, wherein the third time period is between 1 year to 10 years from the second time period.

6. The method of claim 1, further comprising comparing at least two genes of interest selected from the group consisting of nephrin, podocin, synaptopodin, Wilm's Tumor-1 (WT-1), UCH-L1, pax-8, RAP1GAP, Rap1a, RAP1b, beta-1 integrin, CD2-Associated Protein (CD2AP), NEPH-1, ZO-1, alpha-actinin 4, Lmx-1b, Pod-1, podocalyxin, podoendin, FAT, and p-cadherin.

7. The method of claim 3, wherein the expression level is determined by a) a hybridization based method, b) a PCR-based method, particularly a quantitative real-time PCR method, c) determining the protein level, d) a method based on the electrochemical detection of particular molecules, e) an array based method, f) serial analysis of gene expression (sage) and/or g) a rtPCR (reverse transcriptase polymerase chain reaction) of the gene-related mRNA.

8. The method of claim 1, further comprising and measuring the levels of creatinine in the in the first urine sample, and the first time period is before the onset of any cardiovascular disease event is defined by an increase above 20 mcg/gm of creatinine in urine albumin excretion.

9. The method of claim 1, wherein the increase of podocin from the first time period to the baseline is associated with a progressive decline in eGFR.

\* \* \* \* \*